(12) United States Patent
Bonne et al.

(10) Patent No.: US 8,128,873 B2
(45) Date of Patent: Mar. 6, 2012

(54) GAS ANALYZER CASSETTE SYSTEM

(75) Inventors: Ulrich Bonne, Hopkins, MN (US); Gregg M. Swenson, Long Lake, MN (US); Leonard A. Hilton, Buffalo, MN (US); Tom M. Rezachek, Cottage Grove, MN (US)

(73) Assignee: Honeywell International Inc., Morristown, NJ (US)

( * ) Notice: Subject to any disclaimer, the term of this patent is extended or adjusted under 35 U.S.C. 154(b) by 1023 days.

(21) Appl. No.: 11/923,325

(22) Filed: Oct. 24, 2007

(65) Prior Publication Data

US 2009/0111191 A1   Apr. 30, 2009

(51) Int. Cl.
*G01N 7/00* (2006.01)
(52) U.S. Cl. .................. 422/83; 422/82.05; 422/82.11; 436/81; 436/71; 73/761; 356/402; 356/407; 356/437
(58) Field of Classification Search ............... None
See application file for complete search history.

(56) References Cited

U.S. PATENT DOCUMENTS

| 6,393,894 | B1 | 5/2002 | Bonne et al. |
| 7,000,452 | B2 * | 2/2006 | Bonne et al. ............... 73/23.25 |
| 7,746,474 | B2 * | 6/2010 | Oda ............................ 356/402 |
| 2003/0068264 | A1 * | 4/2003 | Schmidt et al. ............ 423/237 |
| 2005/0042136 | A1 * | 2/2005 | Marganski et al. ........... 422/58 |
| 2006/0289809 | A1 | 12/2006 | Bonne et al. |

OTHER PUBLICATIONS http://www.globalspec.com/Supplier/Profile/HoneywellZellweger, Honeywell Analytics, Inc.—Company Profile | Supplier Information, pp. 1-2, printed Feb. 12, 2008.

* cited by examiner

*Primary Examiner* — Sally Sakelaris
(74) *Attorney, Agent, or Firm* — Seager, Tufte & Wickhem, LLC

(57) ABSTRACT

A highly sensitive fluid composition analyzer where a fluid may be placed in contact with a very small area on a material sensitized to change color in the presence of a specific type of compound, to be impinged with light. The light reflected, transmitted and/or scattered by the material may serve as input for the analyzer electronics. The fluid may be preconcentrated prior to being brought in contact with the material. The area on the material may be a spot having an outside dimension of less than one millimeter.

13 Claims, 21 Drawing Sheets

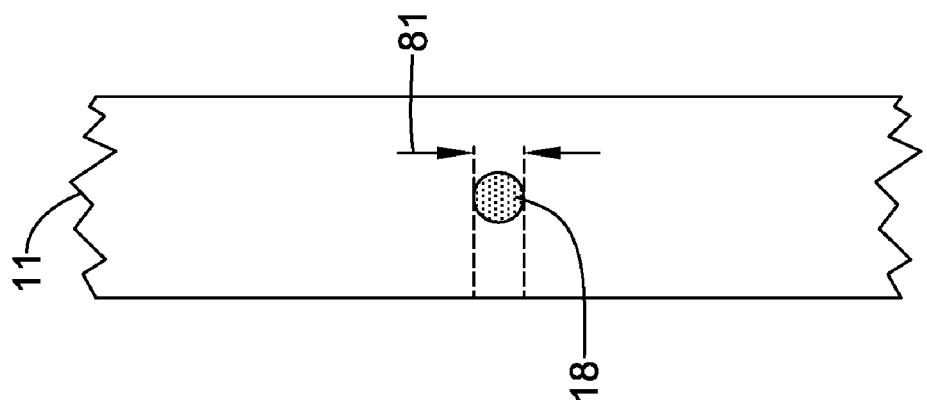

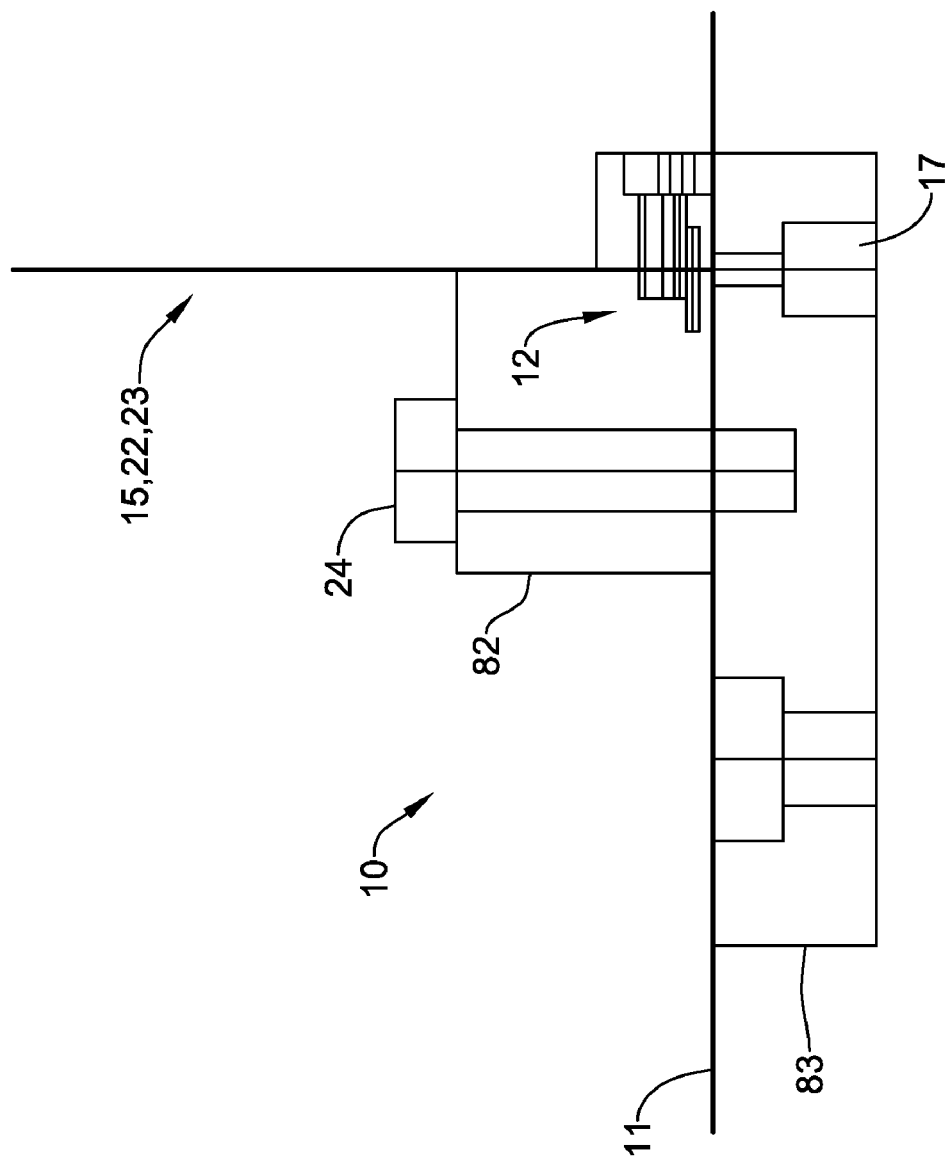

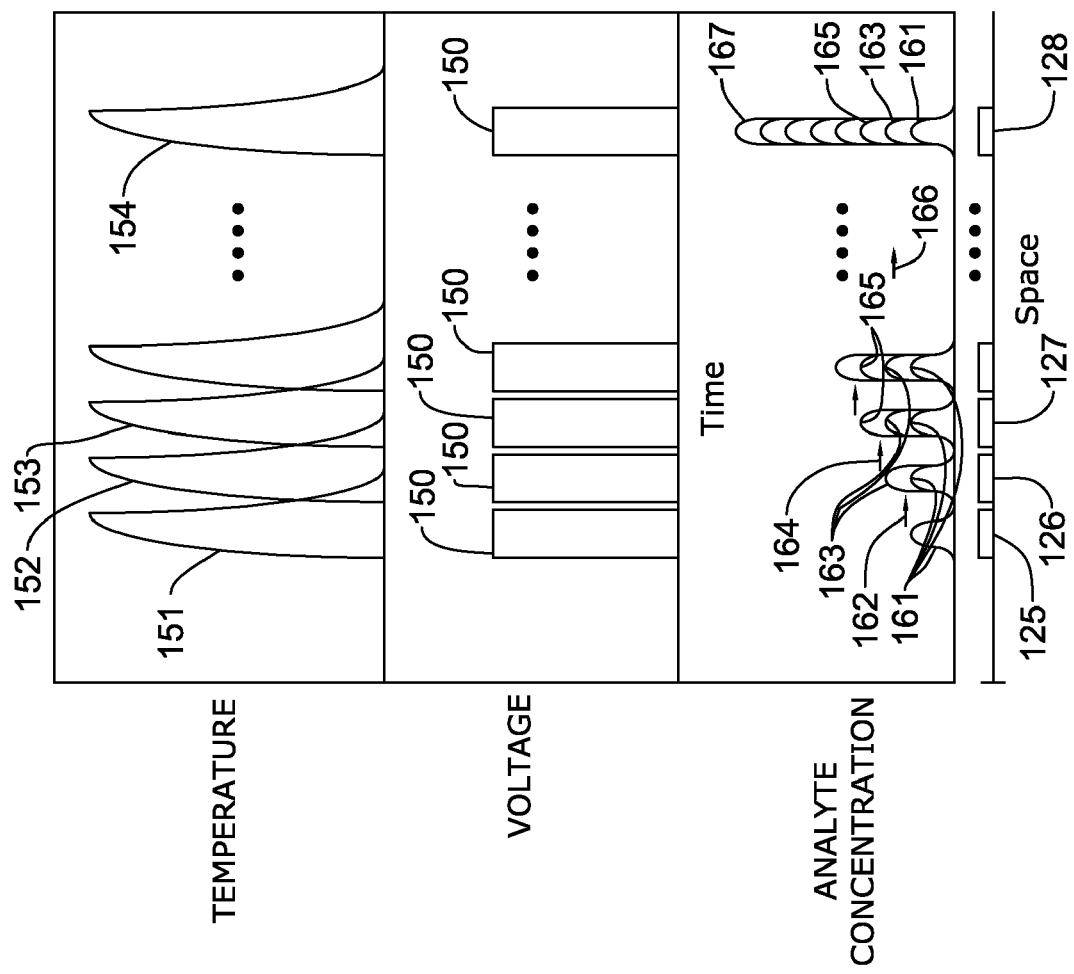

GAS ANALYZER CASSETTE SYSTEM

BACKGROUND

The invention pertains to sensors and particularly fluid composition sensors. More particularly, the invention pertains to sensitive fluid composition analyzers.

SUMMARY

The invention is a highly sensitive analyzer where a fluid may be placed in a very small area on a fluid-composition-sensitive material to be impinged with light and detected for analysis. The fluid may be pre-concentrated prior to being placed on the material.

BRIEF DESCRIPTION OF THE DRAWING

FIG. 1b is a diagram of an analyzer assembly incorporating the holder in FIG. 1a;

FIG. 1c depicts a short piece of a paper tape which may be used in the assembly in FIG. 1b;

FIGS. 2a and 2b are diagrams of side and perspective views, respectively, of a micro-spot paper tape analyzer module;

FIGS. 11-14 show an illustrative example of a pre-concentrator which may be used as an analyte modulator for the present sensor system.

DESCRIPTION

Figure 1A:
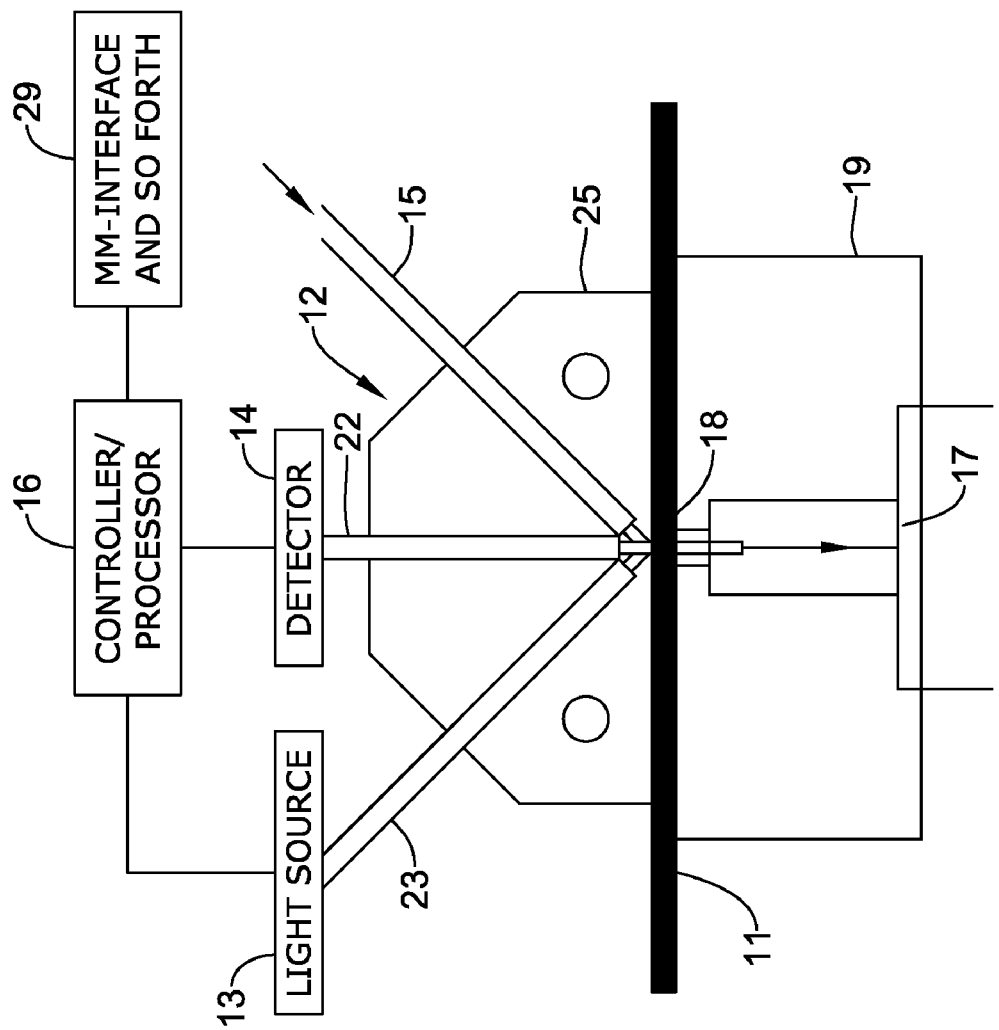
FIG. 1a is a diagram of a fluid-composition-sensitive-paper holder having a gas inlet and outlet, an optical input channel and an optical readout.

Industrial toxic gas monitors as used, for example, in semiconductor processing, should be sensitive (ppb level) and specific. Traditional NDIR analyzers are unwieldy (with meter-long path lengths) if they are to reliably achieve ppb-level sensitivities. Typical GCs and MSs can not achieve such sensitivities. Therefore, a family of analyzers based on color-changing reactions on paper (as with litmus paper) have been offered and accepted in the market for their reliable performance. However, the servicing and material cost of such reagent-bearing paper is a burden that many present customers would rather avoid if a reliable alternative can be found. In addition, some analytes such as $GeH_4$ (Germane), are "slow", i.e., take too much time to be detected at the desired level.

A solution to these shortcomings may be a combination of the following: 1) Make the sample-paper interaction spot very small, so that the use of costly reagent paper is very low, but the mass flux of sample fluid transferred to the spot area, and therefore its speed of detection are large; 2) Preconcentrate the analyte(s) of interest, so that the time needed for detection becomes one in an acceptable range, which is equivalent to an increase in sensitivity; 3) Make the spot size so small that a micro-fabricated adsorber, such as a PHASED chip or the like, can provide the needed analyte preconcentration, and thus minimize the electric power needed for preconcentrator operation; and 4) Reduce preconcentrator action for other analytes to prevent swamping of the detector.

Building on an established paper tape approach (e.g., dry reagent embedded in porous paper changes color upon contact with specific air-borne analyte), an original size of the exposed paper tape spot of about 3 to 4 mm outside dimension (OD) may be reduced by about 42 times to about 0.15 mm or so OD, to permit use of a much smaller sample gas flow. The dimension of spot 18, whether circular or not, should not be much less than 0.1 mm OD in order not to become of the same order of magnitude as the pores or fibers of the paper or reagent host material. The small flow because of the small spot may enable preconcentration of the analyte with little power consumption (during the adsorber heating period).

The system may consist of "channeling" just a pre-concentrated sample towards the paper tape spot, (by splitting a flow from an adsorber into a low-analyte and a high-analyte stream) thus resulting in a reduced paper tape sampling time and/or improved sensitivity to the selected preconcentrated analyte. Furthermore, the system may also feature a low-cost and reliable design of such "channeling," based on the action of valve-less, thermal gas expansion and contraction.

The system may be based on principles of gas adsorption, and gas expansion/contraction. Specific adsorber materials for selected analytes may be known from gas chromatography.

The system may provide a near-term solution to the problem faced to modernize the typical chemical cassette analyzers, versus the longer-term solution of analyzing the color change of liquid reagent droplets directly. The present system may lead to a reduction in the amount of the used reagent paper, faster and/or more sensitive response to selected analytes, while maintaining about the same sensitivity to other analytes. An additional benefit from this approach is that one does not necessarily block the potential use of an adsorber structure, such as PHASED instrumentation and other adsorber designs, but may make the paper tape flow compatible with it, while leveraging the low energy requirements of the adsorber. A PHASED mechanism may be noted herein and in U.S. Pat. No. 6,393,894, issued May 28, 2002, U.S. Pat. No. 7,000,452, issued Feb. 21, 2006, U.S. patent application Ser. No. 11/738,853, filed Apr. 23, 2007, and U.S. patent application Ser. No. 11/762,891, filed Jun. 14, 2007. U.S. Pat. No. 6,393,894, issued May 28, 2002, U.S. Pat. No. 7,000,452, issued Feb. 21, 2006, U.S. patent application Ser.

No. 11/738,853, filed Apr. 23, 2007, and U.S. patent application Ser. No. 11/762,891, filed Jun. 14, 2007, are hereby incorporated by reference.

The system may address prospective customer concerns about a slow response of paper tape to, for example, $GeH_4$ and the high cost of paper tape. The system may reduce the size of the exposed "spot" on the paper tape as a way to reduce the consumption and cost of the paper tape, and to augment this benefit with reducing the analysis time via the use of pre-concentrated analyte, for example, PHASED instrumentation. The smaller spot size may also enable reducing the sample flow typically used with paper tape by about a 180 times, down to ≦1 sccm, which is typical for a PHASED micro gas analyzer (MGA) flow.

A paper tape-based gas sensing system may typically use a spot having an outside dimension (OD) between 2.5 mm and 4 mm. Such system may have a sample flow velocity through a paper 11 of about 9 cm/s, which can also be the flow used for the micro-spot version sensor 10 presented in FIGS. 1a through 4b, so that sample gas pressure-drop pump-load of a system 21 (FIG. 7b) does not need to change with a substitution of the present sensor 10 in lieu of a previous sensor. Analyte reaction with the reagent in the paper may result in a change in color (spot 18), which is detected photoelectrically. Sensor system 10 may have a paper tape 11, an LED light source 13, a photodetector 14, sample gas inlet 15, a sample gas outlet 17 and a spot 18 on paper 11 (FIG. 1a).

Figure 1B:
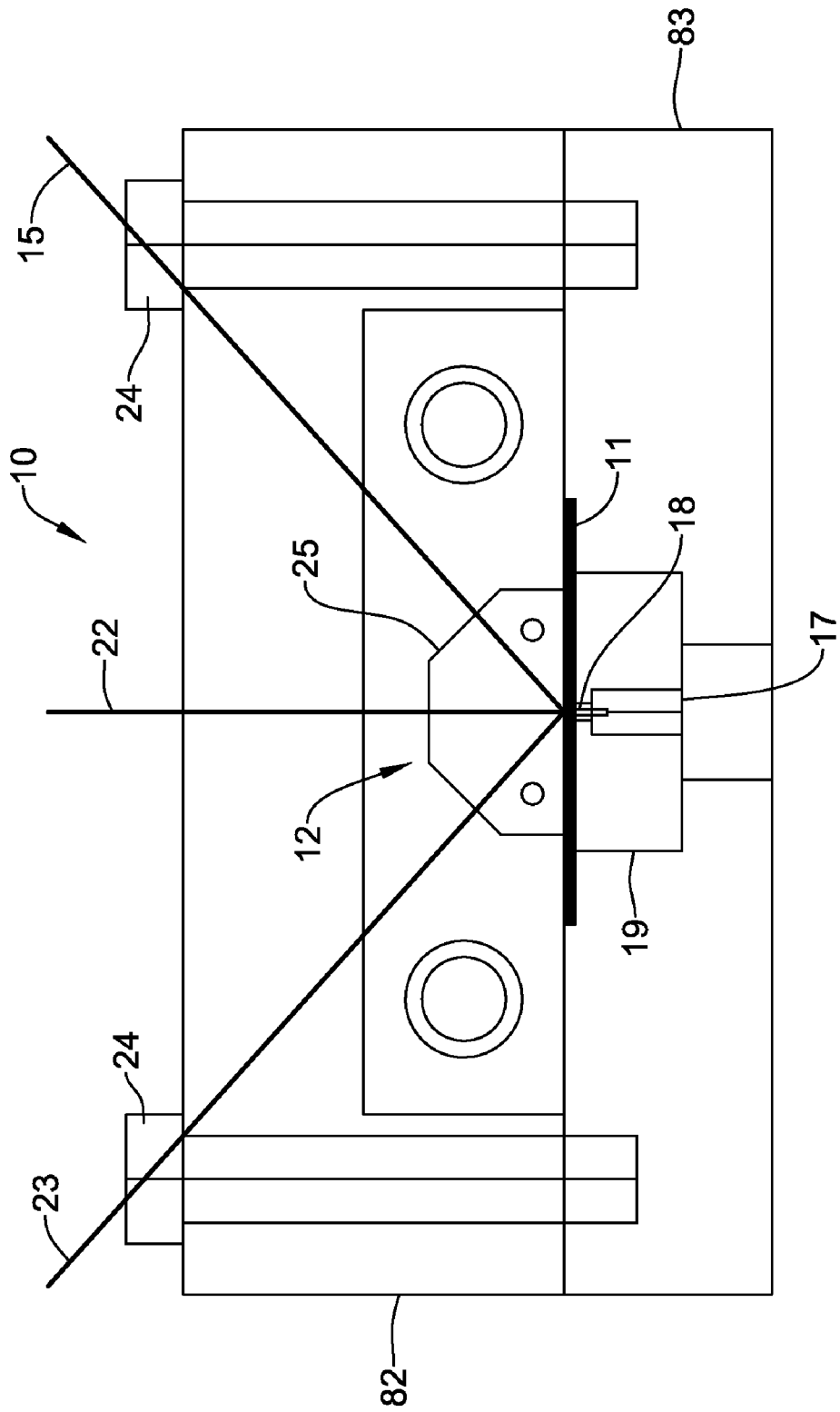

Sensor system 10 may be regarded as a micro-toxic gas analyzer cassette 10. FIG. 1a shows a reagent-paper holder 19, a gas inlet 15 and outlet 17, an optical input channel 23 and an optical readout 22. FIG. 1b shows an assembly of system 10. FIG. 1a reveals how the paper tape 11 is clamped between gas inlet 15 and outlet 17, with an upper structure 25, especially at the point where the light source 13 (via optical fiber or channel 23) illuminates the small spot 18 having an OD 81, as shown on a paper tape 11 in FIG. 1c, and reflects and/or scatters light into the optical fiber or channel 22 leading to the photo detector (PD) 14. Photo detector 14 may output signals that indicate intensity and/or color of the detected light. Detector 14 may be connected to a controller/processor 16, which may provide further analysis of the detector signals. Light source 13 may be connected to controller/processor 16 for reasons of knowing when the source 13 is on or for controlling source 13. Controller/processor 16 may be connected to a module 29 having an MM-interface, and so forth.

Spot 18 may be referred to as a micro spot. The range of dimension 81 may be between 0.1 and 1 millimeter. A nominal size range of spot 18 may be between 100 and 250 microns. Spot 18 may be of various shapes, but likely a close-to-circular shape.

Figure 2B:
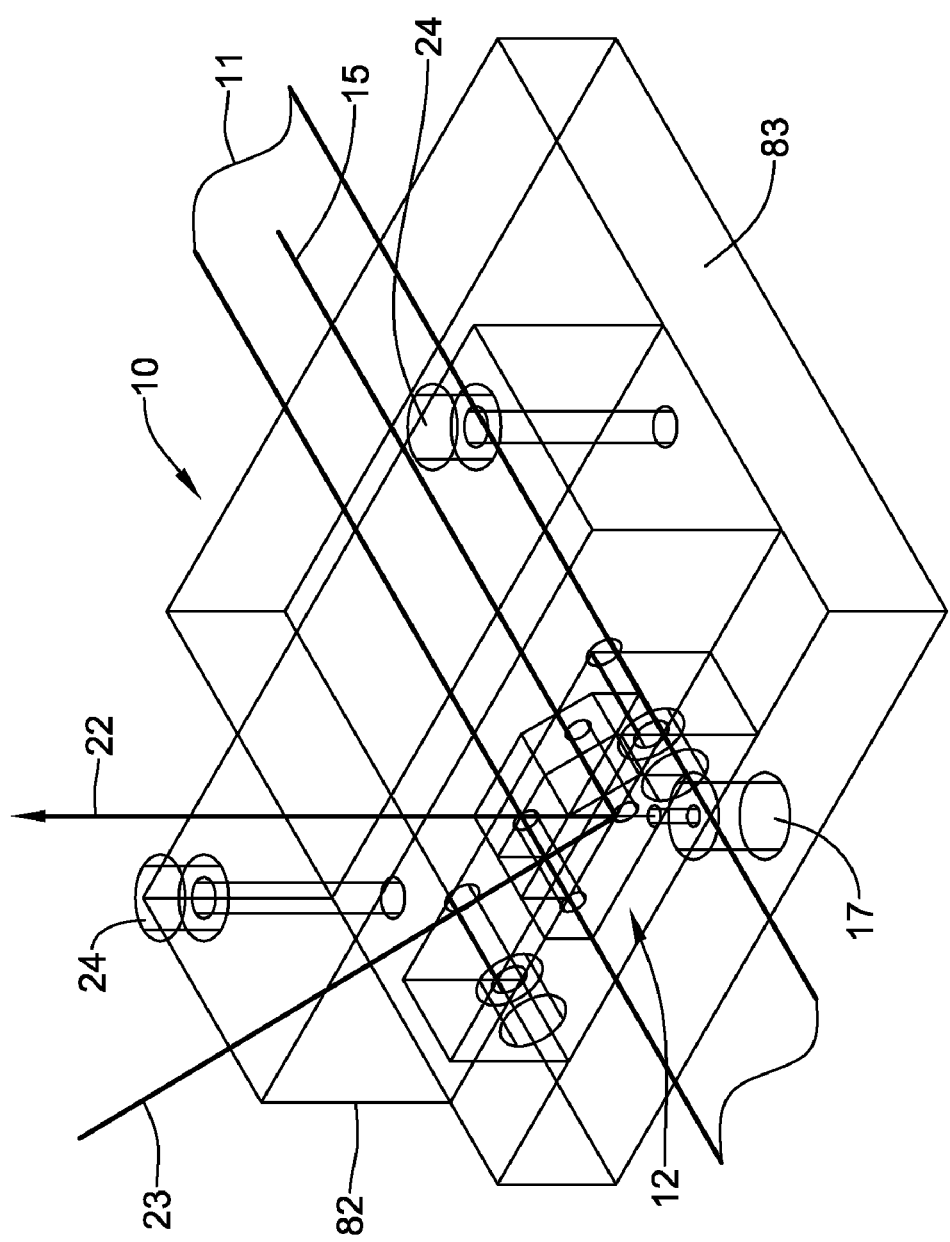

FIGS. 2a and 2b are diagrams of side and perspective views, respectively, of a micro-spot paper tape analyzer module 10, showing a structure 82 containing the structure 25, retaining just enough space for a paper tape 11, being clamped down by two thumb-screws 24 onto a structure 83 containing the base plate 19 for supporting the paper 11.

Figure 3:
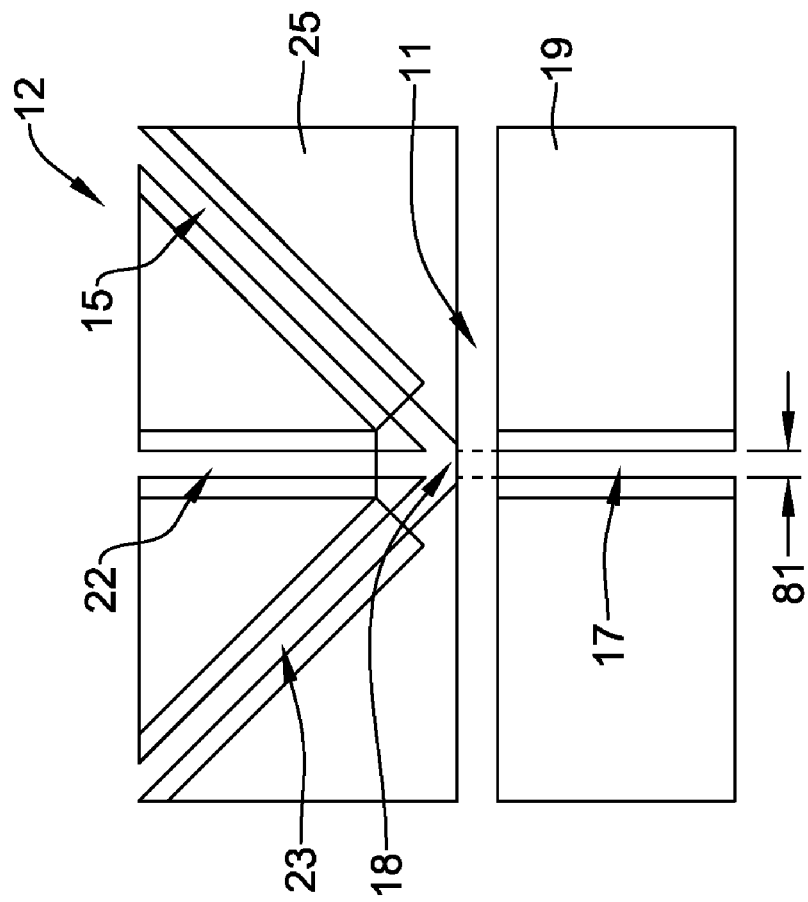
FIG. 3 is a diagram of a magnified portion of the micro-spot paper tape analyzer assembly or system.

FIG. 3 is a diagram of a magnified part of the micro-spot paper tape analyzer assembly or system 10, showing a critical alignment of the optical inlet 23 and outlet 22 fibers or channels over the spot 18 on the paper 11 where the sample gas is to be pumped through. The sample may be brought in through the inlet channel, tube or capillary 15. The sample may exit the analyzer 12 via outlet channel or tube 17. The initial portion of outlet 17 may have a diameter which is the same as the diameter 81 of spot 18. An example diameter may be about 150 microns (0.15 mm). The diameter of a micro spot may vary from about 0.1 to 1 millimeter. At the low end of this range, the spot diameter may be commensurate to the thickness of the paper or material hosting the reagent.

Figure 4A:
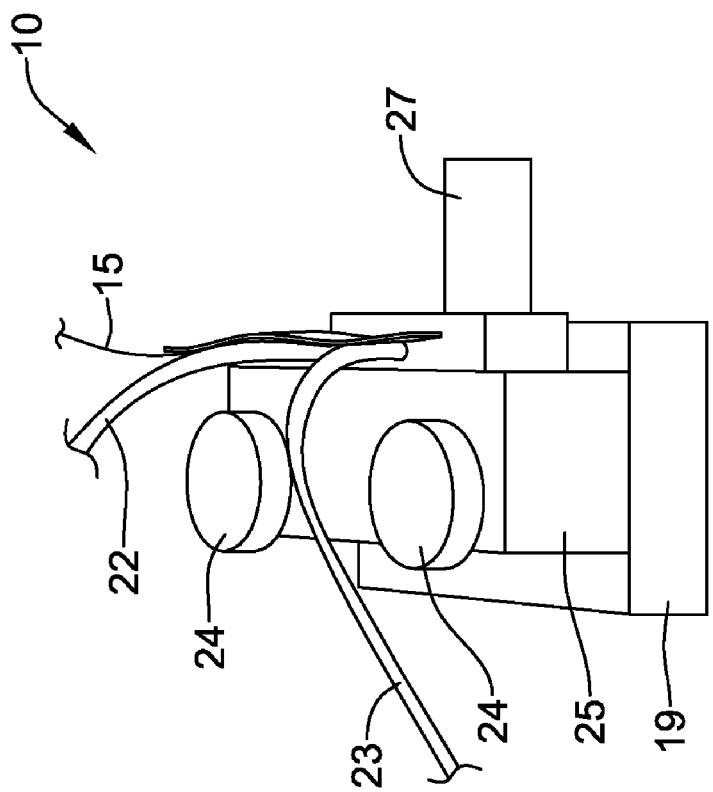
FIGS. 4a and 4b show a fabricated micro-spot paper tape assembly.
Figure 4B:
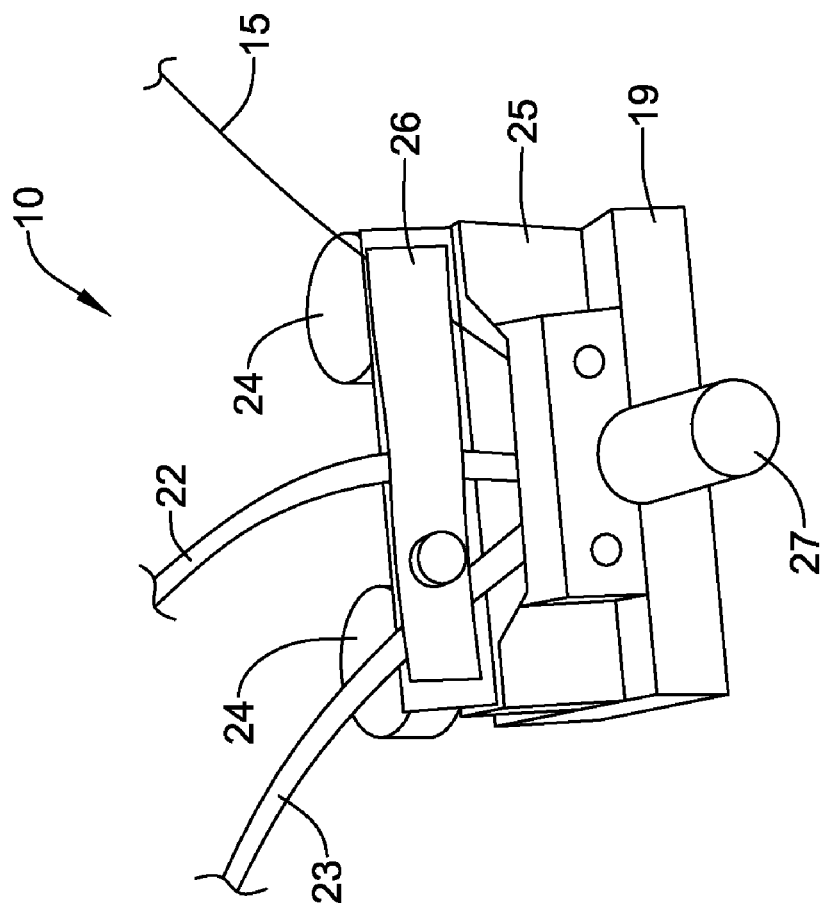

FIGS. 4a and 4b show a fabricated micro-spot paper tape assembly or system 10 example. The shown white-head thumbscrews clamp down the (not yet inserted) paper tape 19. The optical fibers 22 and 23 (with cladding and outer sheath) as well as the gas inlet capillary 15 are held in place by a strip 26 of aluminum. A black knob 27 is a handle that was used to hold a plastic insert of the assembly while being machined.

Figure 5A:
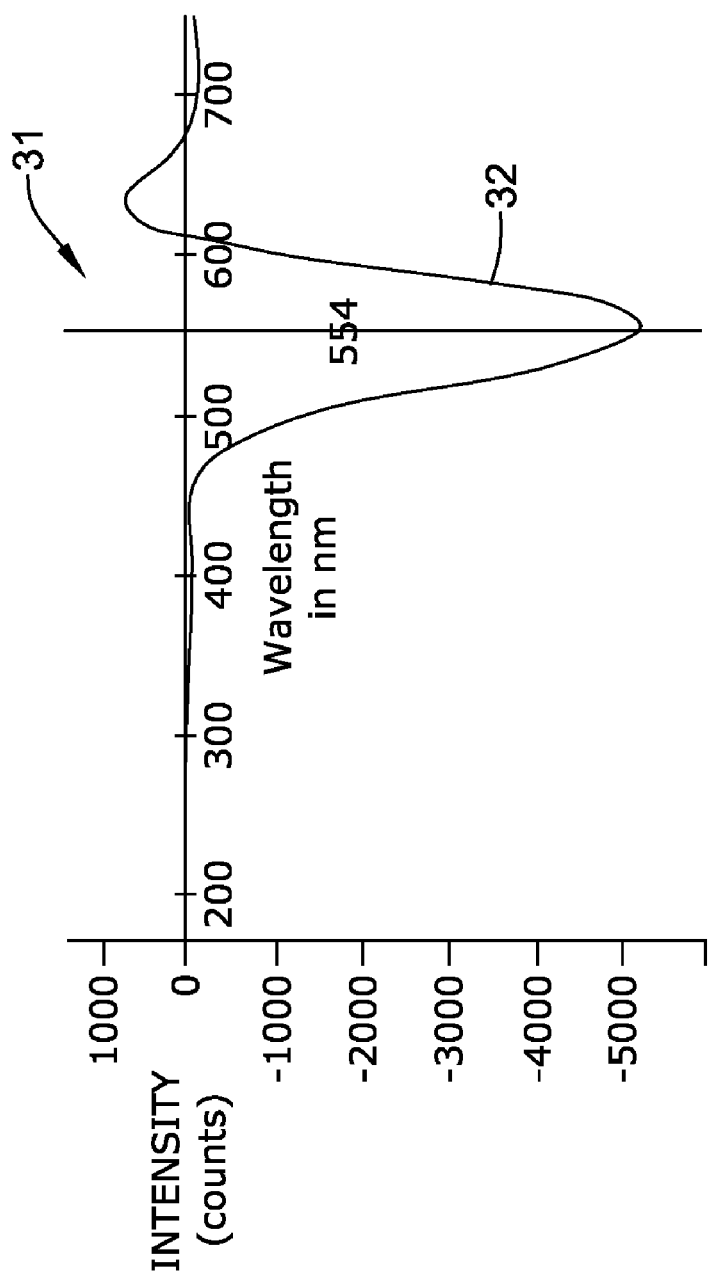
FIG. 5a is a graph of the spectral change of material paper after exposure to a fluid, which causes the material to change in color, as indicated by intensity counts versus wavelength in nanometers.
Figure 5B:
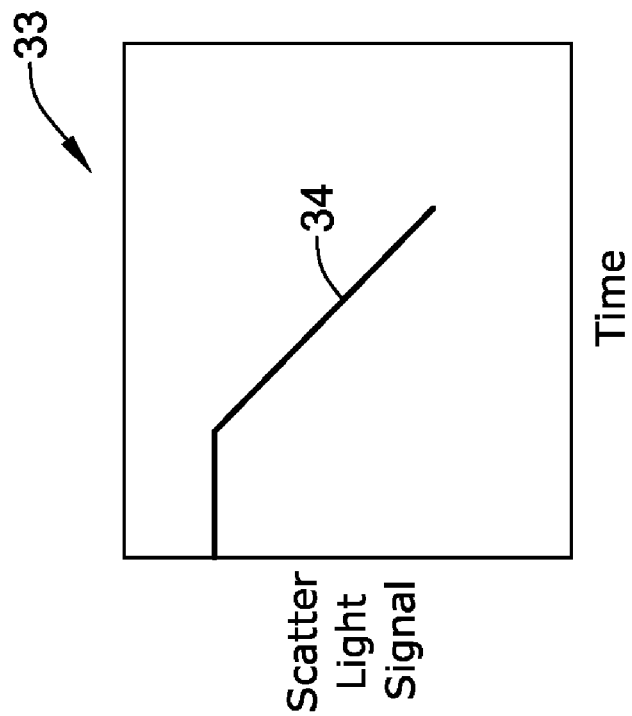
FIG. 5b is a graph of a drop in a photo detector light signal from paper 11 versus time of exposure of the paper to analyte and its associated change in color.

FIG. 5a is a graph 31 of the spectral change of sensitized material paper after exposure to a fluid-component, which causes the material to change in color, as indicated by intensity counts versus wavelength in nanometers. For example, graph 31 of the spectral change (intensity curve 32) may be of "hydride paper" after exposure to ammonia, which caused the paper to turn pink. Detection may be via a 0.6 mm optical fiber leading to an OceanOptics™ spectrometer. FIG. 5b is a graph 33 of a drop in a photo detector light signal decrease with time (curve 34) as paper 11 is exposed to analyte and changes color.

Figure 6A:
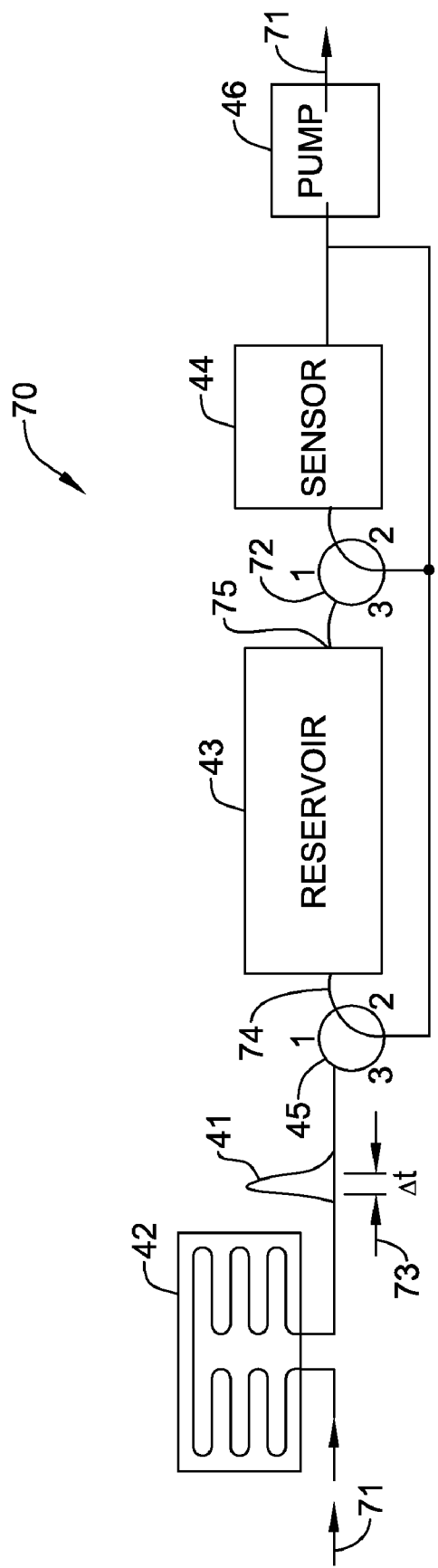
FIG. 6a is a diagram of a two-valve sensor system having an absorber as pre-concentrator analyte modulator arrangement with a reservoir.

FIG. 6a may present an approach 70 based on the combination of a pre-concentrator (PC) 42 with a storage reservoir 43, into which several injection pulses of PC'd analyte 71 can be made. System 70 of FIG. 6a may solve a problem of non-commensurate response times between PC 42 and sensor 44 by using a reservoir 43 and valves 45 and 72. FIG. 6a is a diagram of pre-concentration arrangement for a sensor 44 with large dead volumes. One may first purge reservoir 43 and sensor 44 with valves 45 and 72 having positions 1,1, respectively. Second, the reservoir 43 and sensor 44 may be evacuated with valve 45 and 72 positions, respectively, 2,3, 2,2 or 2,1. Third, the PC 42 sampling time may be taken with positions 3,2 of valves 45 and 72, respectively. Fourth, the analyte 71 in PC 42 may be desorbed while valves 45 and 72 having positions 3,2, respectively. Fifth, a PC 42 analyte 71 pulse 41, having a width of a delta time (Δt) 73, may be injected into reservoir 43 with valves 45 and 72 having positions, respectively, 1,2 or 1,3 (for a few milliseconds). The first through fifth steps may be repeated until reservoir 43 is filled. Sixth, the analyte from reservoir 43 may be measured with positions 1,1 of valves 45 and 72, respectively. One may continue by returning to the first step.

A PHASED chip may be used as a PC 42, e.g., with its elements connected in series, as shown, to maximize the analyte concentration gain, or some elements in parallel if increasing the volume of the output pulse is also important. Alternatively, a small, heatable, stainless (or other material) tube coated or packed with Tenax™ on its internal walls of the PC 42, may be used as a preconcentrator and modulator in FIG. 6a. The reservoir 43 may be fashioned as simple empty containers of volume commensurate with the dead-volume of the sensor 44. But the containers may also feature some loose packing in a long tube that would enable the volume of the repeatedly injected analyte pulses 41 to gradually progress from an inlet 74 towards an outlet 75 in the manner of a so-called "plug-flow", and thus reduce mixing of the injection-pulse analytes with the main carrier fluid and/or require less of a vacuum at the start of the process. In addition, another approach is that the second valve 72 (between the reservoir 43 and the sensor 44) may have an opening to the ambient or sample fluid, so that the fluid may be sampled by the sensor 44 directly, without the need for pre-concentration, in a situation where the analyte 71 concentrations are much higher than needed for a minimum detection limit (MDL).

Figure 6B:
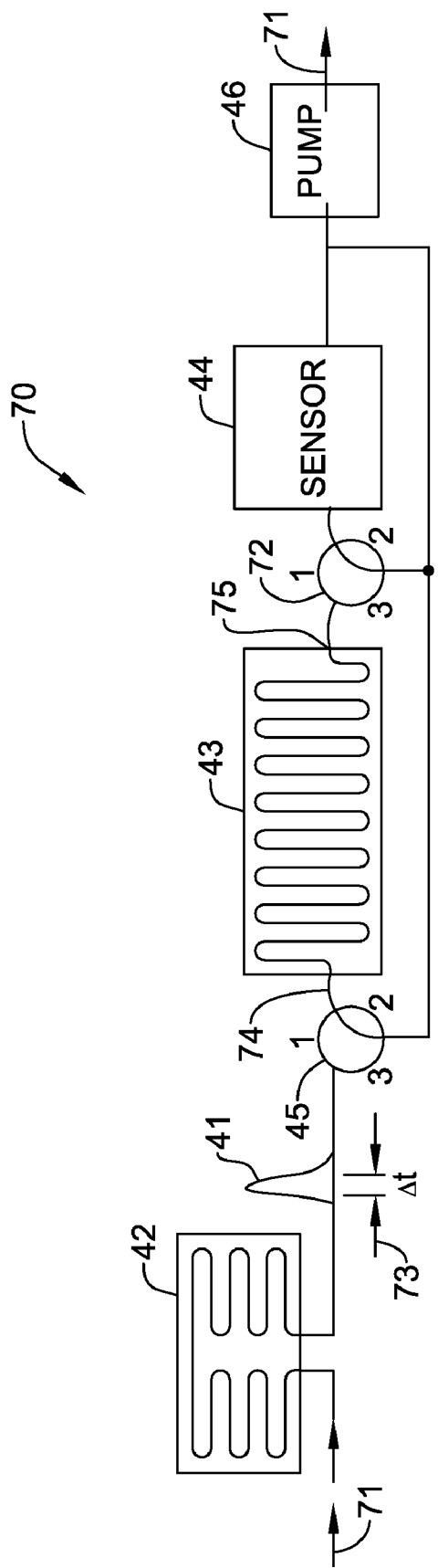
FIG. 6b is a diagram of the two-valve sensor system having the absorber/pre-concentrator analyte modulator arrangement with a reservoir having a long tubular shape.

FIG. 6b shows another version of the sensor system 70 with an input sample 71 of about 10 mm³/sec to the modulator 42 which is connected to reservoir 43 as in FIG. 6a. FIG. 6b shows reservoir 43 having a long tubular shape to minimize mixing of new analyte pulses with previous pulses 41, while still facilitating an increase of sensitivity of the detector or sensor 44, due to the increased concentration of analyte from the modulator 42. In other words, the reservoir 43 may have the shape of a long and narrow tubing to minimize mixing of new gas with old gas.

Figure 7A:
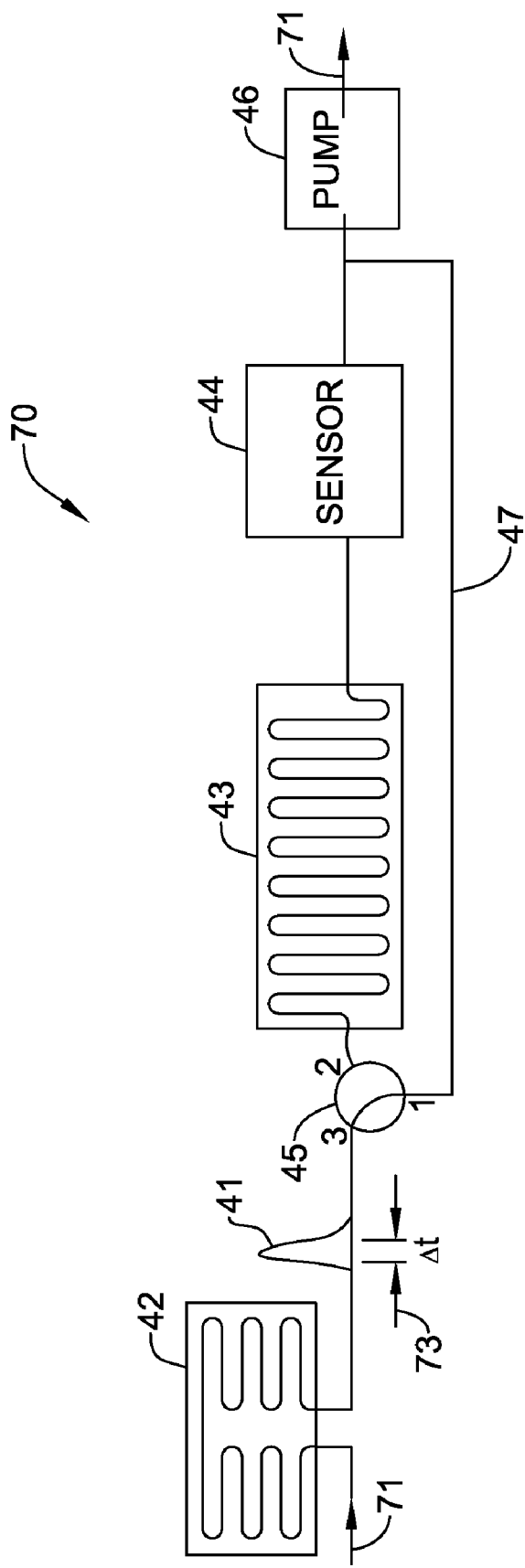
FIG. 7a is a diagram of a one-valve version of the sensor system in FIG. 6b.

FIG. 7a is a diagram of an apparatus 70 having one valve and indicating how analyte pulses 41 desorbed by an adsorber 42 (e.g., PHASED) are led towards the reservoir 43 and sensor 44 by briefly switching the valve 45 from the normal valve position of 3-1 to position 3-2 and back, to have only the peaks flow through the flexible-volume reservoir 43, when they pass that valve 45. The total flow of 0.6 cm$^3$/min being "on" all the time may be effected by pump 46 whether through the reservoir 43 and sensor 44, or bypass line 47.

Figure 7B:
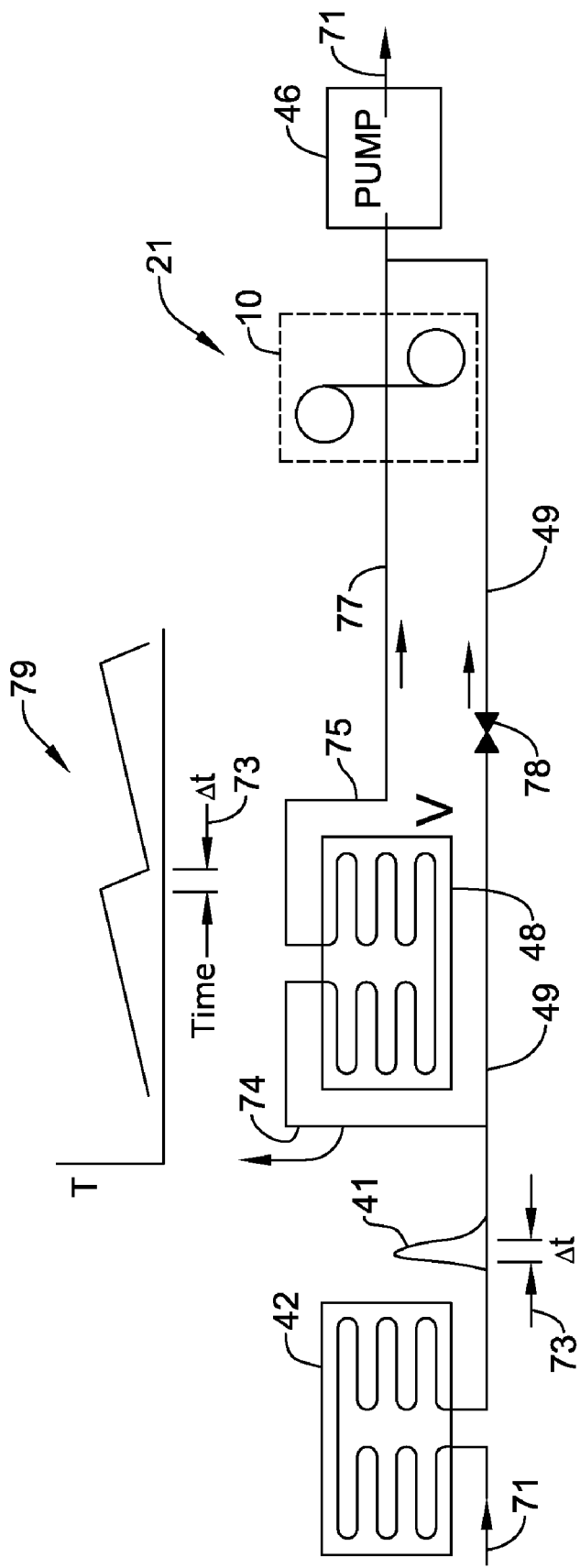
FIG. 7b is a diagram of a sensor system like that of FIG. 7a in which the reservoir and valve has been replaced by a rapidly heatable reservoir.

FIG. 7b is a diagram of a valve-less approach of a sensor system 21 in which the reservoir 43 and valve 45 have been replaced by a rapidly heatable reservoir 48, which pulls each pre-concentrated Δt-peak 41 into a "high concentration path" by way of suitably synchronized slow heating and rapid cooling periods. An output of reservoir 48 may provide about 0.9 mm$^3$/sec concentration flow through line 77 to the paper tape sensor system 10. Bypassing input 74 of reservoir 48 may be a low concentration 9 mm3/sec flow through line 49 to pump 46 via a restriction 78. The restriction 78 in the low-concentration bypass adjusts the flow, so that (in this example) the high-concentration flow in line 77 may be about 10 times smaller than the bypass flow in line 49.

During soaking and PC (pre-concentration) time, the reservoir 48 gas temperature may rise and expand (graph 79) to prevent low concentration gas from entering. As to volume (V) dynamics of reservoir 48, a peak volume may be VΔt/10 and the reservoir volume may be VΔt. The reservoir 48 "suction" pump rate (during rapid gas cooling) may be minus 10 mm$^3$/sec for a time of about 1 Δt and the "expansion" rate (slow heating) may be plus 1 mm$^3$/sec for a time of about 10 Δt.

It may be said that the valves can be absent in the system 21 of FIG. 7b since, in lieu of valve 45 and reservoir 43 of FIG. 7a, there is a reservoir 48, V, which is a heatable version with a similar long and narrow tube, which can be operated (by cooling and heating) to draw the modulator gas pulse 41 into the reservoir 48 when rapidly cooled, and slowly heated to expand the gas to match the sample flow rate to the pump 46, and have a substantially zero flow rate input from the modulator or pre-concentrator 42 during the time when the modulator is in its adsorption period or mode.

Again, during soaking and PC time, the gas temperature in volume, V (reservoir 48), may rise (graph 79) and expand to prevent low concentration gas to enter. When the analyte peak passes the "T", the gas is allowed to rapidly cool and contract, thereby drawing or pulling the peak 41 into V 48. The average flow rates may be 0.9 mm$^3$/sec of high concentration gas in line 77 and 9 mm$^3$/sec of low concentration gas in bypass line 49, as indicated, and represent a PC gain of analyte concentration of ten times. The total flow of the sample 71 at the input of the pre-concentrator or modulator 42 may be approximately 0.6 cm$^3$/min or 10 mm$^3$/sec.

To achieve such or similar concentration gains, the "duty cycle" (cold/hot time ratio) of the adsorber 42 needs to equal that gain, and be supported by analyte "breakthrough" times that are greater than the chosen "cold" adsorbing time. A low concentration bypass 49 may be between the input of volume 48 and the input of pump 46. In the present example with a time ratio (which correlates with the concentration gain) of 10/1, the flow ratio bypass/high-concentration may also be at the value of 10/1, as indicated in FIG. 7b.

In sum, the reservoir in FIG. 7a is filled with concentrated analyte via a conventional valve 45 may switch the flow of the analyte peak 41. The FIG. 7b shows a way of accomplishing the same thing, i.e., directing the flow of the analyte peak 41, but using thermal gas expansion pulses, as used with thermal micro-pumps.

Aspects of the present system 21 with the sensor 10 may include splitting the flow from an adsorber device 42 into a "low-analyte" concentration or waste stream and an "enriched analyte" stream. The enriched stream may be channeled towards a sensor (EC or paper tape 10) in order to generate a stronger sensor signal, and to achieve a more rapid sensor response. The split flow may be used with an integrating sensor, such as the paper tape sensor system 10. The size of the paper spot may be reduced so much (a reduction of about 42 times in the diameter, to about 0.1 to 0.3 mm) in that sufficient flow can be provided by a micro gas chromatography (GC) adsorber, such as PHASED 42, and the concentration of analyte in the flow stream can be (2 to 10 times) more concentrated or enriched.

One or two valves 3-way valves may be used. The second valve may be located upstream of the sensor 44 to enable exposing the sensor to "zero analyte" condition. The second valve is shown in FIGS. 6a and 6b but not in FIGS. 7a and 7b. The 3-way valve 45 may be replaced with a heatable gas channel or volume 48, which can control the gas temperature to rapidly cool and contract, thereby pulling the desorbed peak towards the sensor stream, and slowly expand to provide the flow towards the sensor 10 and prevent "low-analyte" gas to enter this stream. The adsorber film or packing material may be selected to favor one analyte over others and thus make the sensor more sensitive to that specific analyte. Control of the sample stream valve may be set in such a way that it either maximizes the sensitivity of the sensor 44 or 10, or reduces its sensitivity (to prevent swamping) if the analyte concentration is too high.

Advantages of the present analyzer over other chemical cassette analyzers may include faster and/or more sensitive (about 10 times) detection of analytes. This improvement of speed and/or sensitivity may be accomplished with an added selectivity feature (besides the one associated with the semi-specific chemistry of the paper tape) provided by the chosen nature of the adsorber (polar or non-polar; favoring small or large molecules . . . ) film/packing materials. Paper tape 11 consumption and cost may be reduced by about 40 times. Sample gas stream control may be provided that can either use one 45 or two conventional valves or a more reliable valve-less approach 48 to accomplish the sample gas stream splitting function.

From the flow rates needed for a chemical cassette analyzer (180 cm$^3$/min for 6 min to sense GeH4 at the needed concentration), 10 times that amount may be needed to pre-concentrate with a gain of 10 times. That could correspond to 1800 PHASED chips working in parallel at 1 cm$^3$/min each, while drawing a 10 times higher mass flow. However, a reduction the paper spot area by 1800 times or the diameter by 42 times (i.e., a 150 micron diameter), a PHASED-pumped and 10 times-concentrated flow of 0.1 cm$^3$/min over the smaller diameter, with the same mass flux as before, should increase the response by 10 times (i.e., shorter time or greater sensitivity). The sample velocity through the old conventional paper may be about 180/60 cm$^3$/s/($\pi(0.25*2.54)^2/4$)=9.5 cm/s. The velocity of the present paper 11 may be about 0.1/60 cm$^3$/min/($\pi 0.015^2/4$)=9.5 cm/s, i.e., can be pumped with the same pump.

A test with the assembly 10 of FIGS. 5a and 5b, with its role as the "paper tape sensor" in FIGS. 7a and 7b, may be conducted with a sample of about 75 ppm of ammonia in air, which can result in measurable decay of scattered light intensity, as predicted. The light may be from a He—Ne laser.

Figure 8:
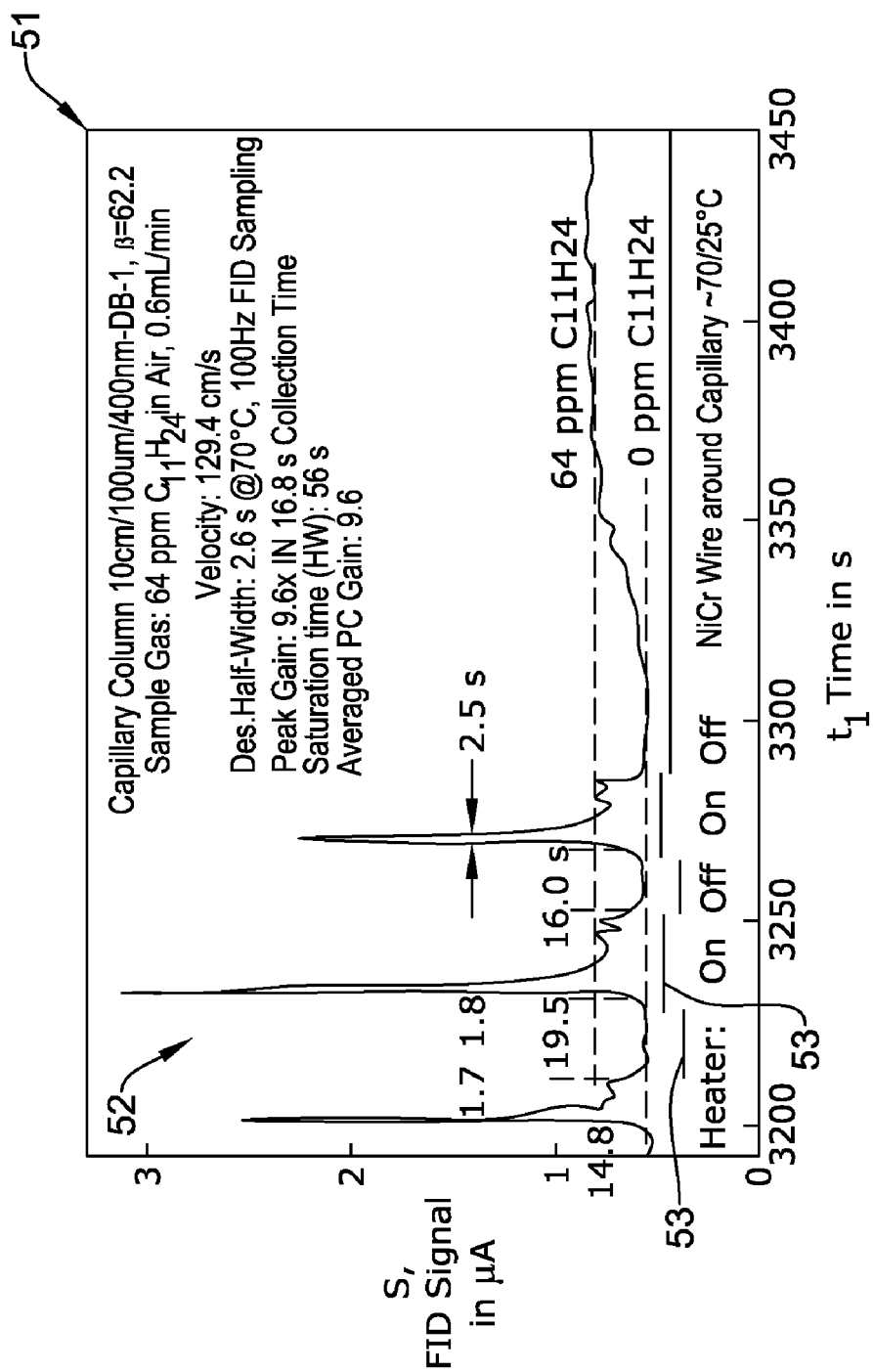
FIG. 8 shows experimental data of an FID signal in microamps versus time in seconds, demonstrating several pre-concentration cycles with an absorber film inside a 10-cm capillary.

FIG. 8 and graph 51 shows some elements of the reduction to practice of the present system, such as an ability to generate analyte concentration pulses 52 of amplitude greater than the concentration in the sample gas, for undecane as analyte. Graph 53 of FIG. 9 shows results with ammonia (=analyte) adsorbed/desorbed in a heatable, short stainless steel capillary.

FIG. 8 shows the graph 51 of an FID (spectrometer, flame ionization detection) signal in microamps versus time in seconds. Graph 51 reveals a generation of analyte concentration pulses or modulation 52, using a 10 cm/100 μm/400 nm DB-5-coated capillary, and a 64 ppm undecane(=analyte)-in-air sample gas flowing at 129.4 cm/s, leading to a 56 sec breakthrough time. The heater on and off periods are indicated by lines 53. The dashed lines mark the FID signal position for sample gas with the input analyte concentration of 64 ppm and with ~0 ppm, right after desorption, for a time needed to readsorb analyte into the DB-5 coat.

Figure 9:
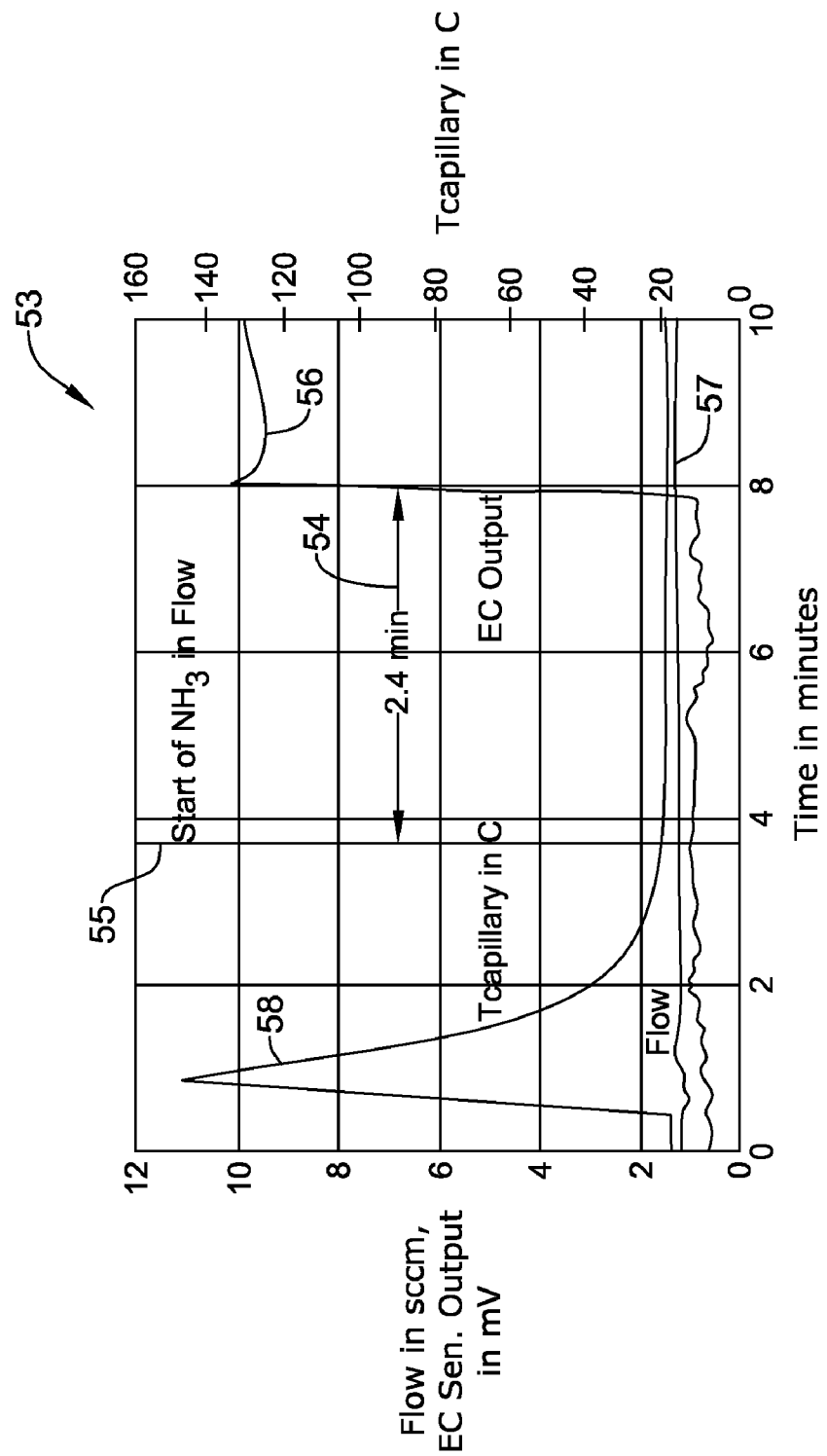
FIGS. 9 and 10 are experimental data of retention time of ammonia in air, measured in millivolts from an electrochemical cell, while keeping track of flow and capillary temperature.

FIG. 9 shows a graph 53 of flow in sccm (cubic centimeters per minute at standard temperature and pressure (stp)), EC (electrochemical) sensor output in millivolts and capillary temperature in degrees C. versus time in minutes. Graph 53 reveals an adsorption and breakthrough of $NH_3$ in a 28.5 cm/0.53 mm ID (inside diameter) SS (stainless steel) capillary packed with Hayesep "P" μspheres. The measured breakthrough time 54 shown as 2.4 min between the start of $NH_3$ in flow 55 and EC output signal 56. Curve 57 represents the flow and curve 58 represents the T capillary in degrees C. With the used flow of about 1.3 sccm and "flow-through" time of 0.019 min (assuming a conservative void fraction of as much as 40 percent), the breakthrough occurs only after 124 "sample gas changes." The $NH_3$ concentration may be about 60 ppm, but its value may not necessarily influence the above breakthrough time. As intended, this breakthrough time appears larger than the 60 to 100 sec response time of an EC cell, and much larger than PHASED breakthrough times.

Figure 10:
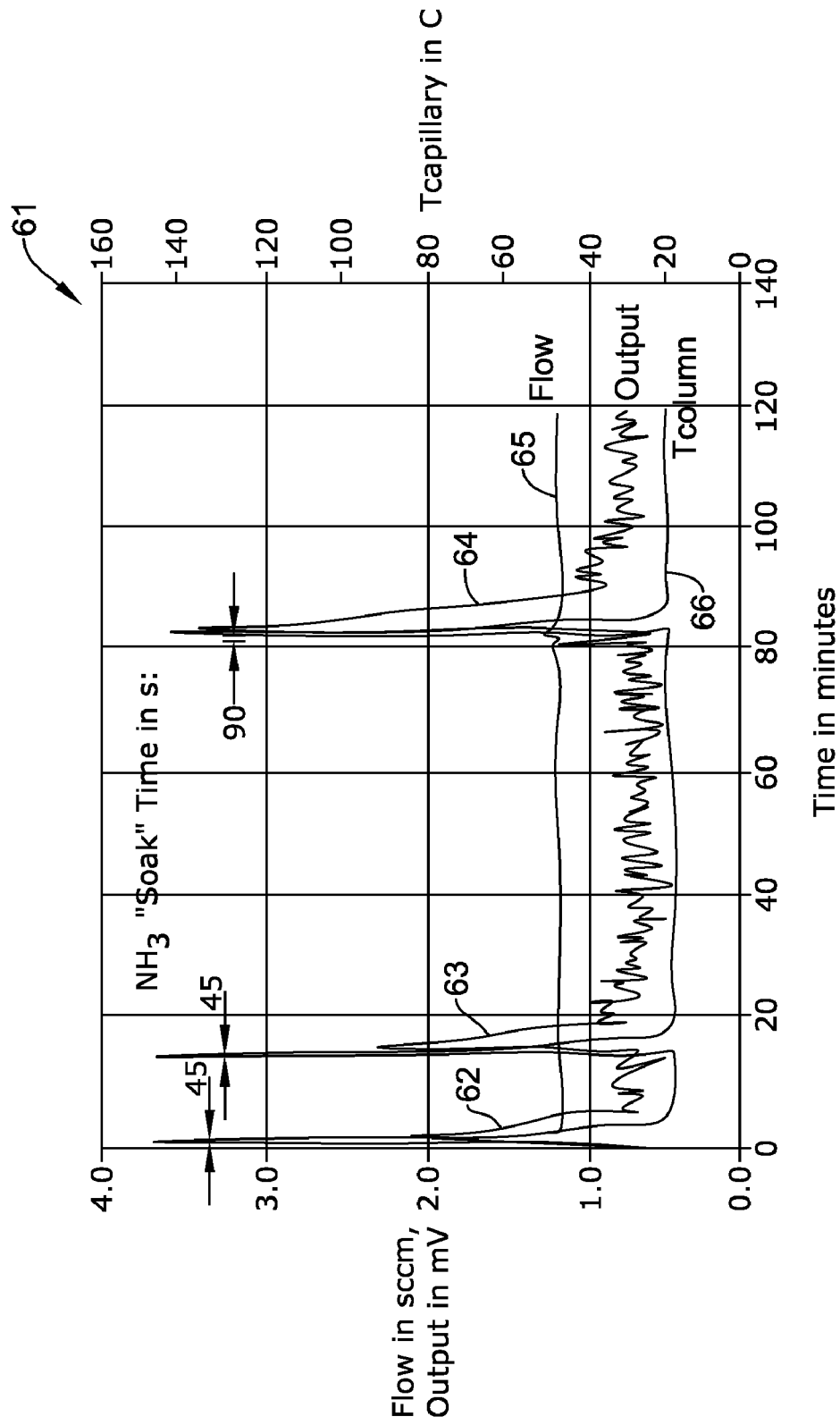

FIG. 10 is a graph 61 of flow in sccm, output in millivolts and capillary temperature in degrees C. versus time in minutes. Graph 61 reveals the generation of analyte (NH3) concentration pulses or modulation, with a 28.5 cm/0.53 mm ID SS capillary packed with Hayesep "P" μspheres. Shown are three sensor output pulses 62, 63 and 64. Pulse 62 reveals desorbed impurities in bottled air (to which the EC sensor is sensitive to), after sampling and soaking bottled air for only 45 seconds. Pulse 63 reveals desorbed $NH_3$, after sampling and soaking dilute $NH_3$-in-air for 45 seconds, and then switching back to air. Pulse 64 reveals desorbed $NH_3$, after sampling and soaking dilute $NH_3$-in-air for 90 seconds, and then switching back to air. These results appear to verify that such adsorber increases pulse amplitude with soak time, as expected. Air flow 65 was maintained at about 1.2 sccm. Also shown is column or capillary temperature 66 in degrees C.

Figure 11:
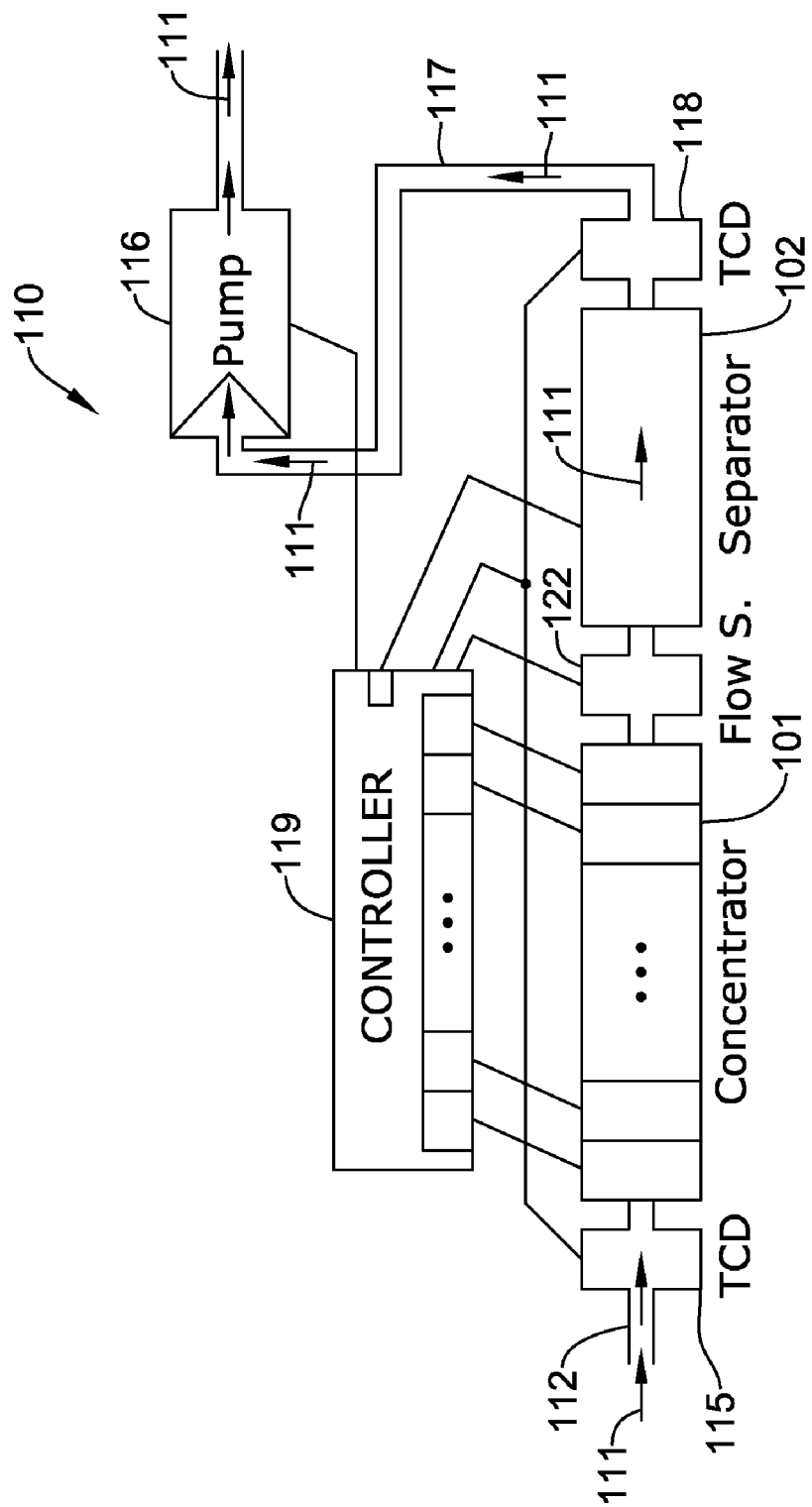

A further approach of an analyte micro-modulator may also be described herein. In FIG. 11, a portion of a fluid analyzer (i.e., PHASED) may be used for an analyte modulator 42 in conjunction with the sensor system 21 which can include a channel or channels for a flow of a sample along a membrane that supports heaters and a stationary phase for sample analysis. The channel or channels may be an integral part of the micro fluid analyzer. The analyzer may have the pre-concentrator (PC) 101 (i.e., like that of PC 42) and chromatographic separator (CS) 102 which incorporates the channel or channels. FIG. 11 is a system view of an example fluid analyzer which may be a phased heater array structure for enhanced detection (PHASED) micro gas analyzer (MGA) 110. It reveals certain details of the micro gas apparatus 110 which may encompass the specially designed channel described herein. The PHASED MGA 110, and variants of it, may be used for various fluid chromatography applications.

Sample stream 111 may enter input port 112 to the first leg of a differential thermal-conductivity detector (TCD) (or other device) 115. A pump 116 may effect a flow of fluid 111 through the apparatus 110 via tube 117, though pump 116 may be a thermal pump or be replaced by a thermal pump. There may be additional pumps, and various tube or plumbing arrangements or configurations for system 110 in FIG. 11. Fluid 111 may be moved through a TCD 115, concentrator 101, flow sensor 122, separator 102 and TCD 118. Controller 119 may manage the fluid flow, and the activities of concentrator 101 and separator 102. Controller 119 may be connected to TCD 115, concentrator 101, flow sensor 122, separator 102, TCD 118, and pump 116. The pump 116 may be a thermal pump or be replaced with a thermal pump integrated in the concentrator 101 or separator 102. Data from detectors 115 and 118, and sensor 122 may be sent to controller 119, which in turn may process the data. The term "fluid" used herein may refer to a gas or a liquid, or both.

Figure 12:
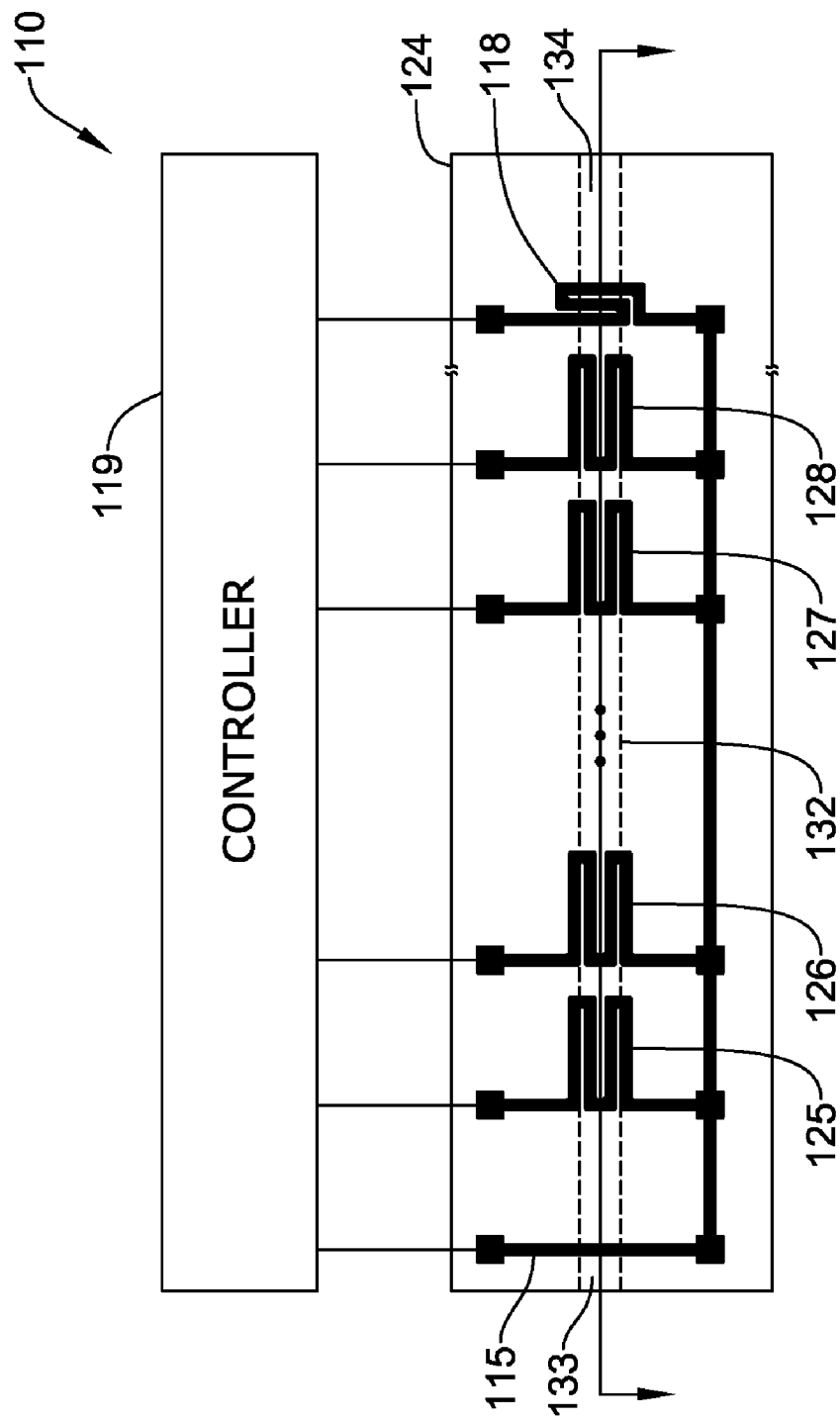

FIG. 12 is a schematic diagram of part of the sensor apparatus 110 representing a portion of concentrator 101 and/or separator 102 in FIG. 11. This part of sensor apparatus 110 may include a substrate or holder 124 and controller 119. Controller 119 may or may not be incorporated into substrate 124. Substrate 124 may have a number of thin film heater elements 125, 126, 127, and 128 positioned thereon. While only four heater elements are shown, any number of heater elements may be provided, for instance, between two and one thousand, but typically in the 20-100 range. Heater elements 125, 126, 127, and 128 may be fabricated of any suitable electrical conductor, stable metal, alloy film, or other material. Heater elements 125, 126, 127, and 128 may be provided on a thin, low-thermal mass, low-in-plane thermal conduction, membrane or support member 124, as shown in FIGS. 12 and 13.

Figure 13:
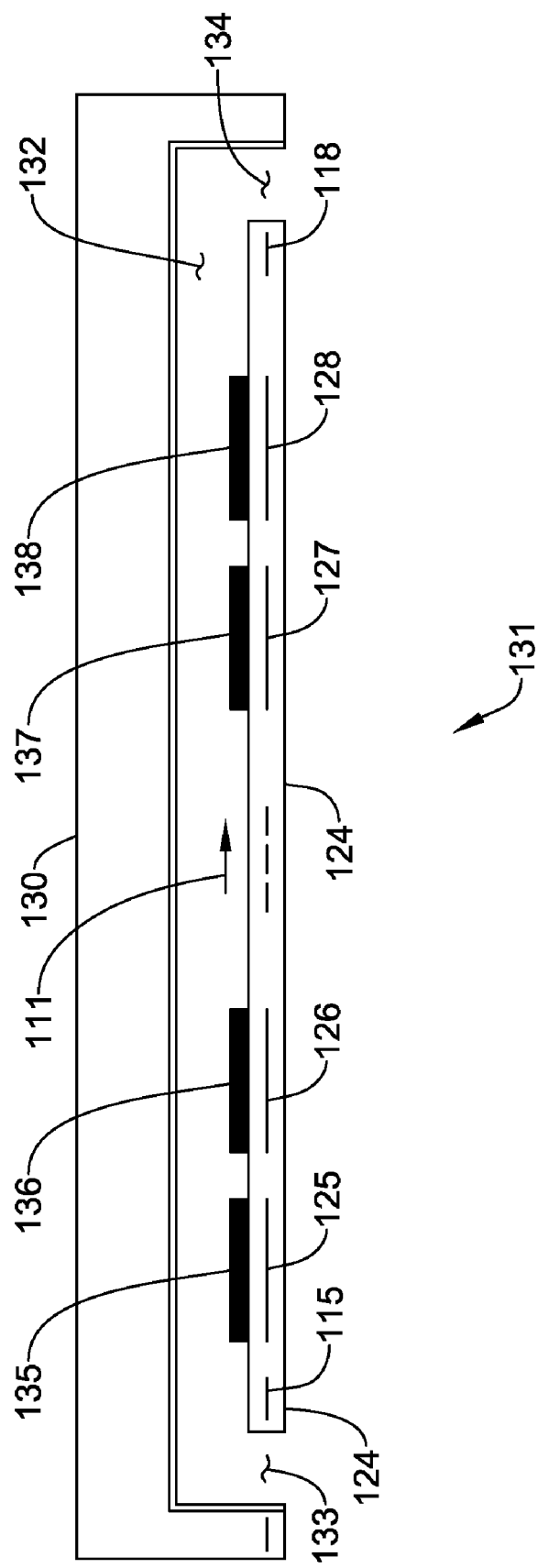

Substrate 130 may have a well-defined single-channel phased heater mechanism 131 having a channel 132 for receiving the sample fluid stream 111, as shown in FIG. 13. The channels may be fabricated by selectively etching silicon channel wafer substrate 130 near support member 124. The channel may include an entry port 133 and an exhaust port 134.

The sensor apparatus 110 may also include a number of interactive elements inside channel 132 so that they are exposed to the streaming sample fluid 111. Each of the interactive elements may be positioned adjacent, i.e., for closest possible contact, to a corresponding heater element. For example, in FIG. 13, interactive elements 135, 136, 137, and 138 may be provided on a surface of support member 124 in channel 132, and be adjacent to heater elements 125, 126, 127, and 128, respectively. There may be other channels with additional interactive film elements which are not shown in the present illustrative example. The interactive elements may be formed from any number of films commonly used in liquid or gas chromatography. Furthermore, the above interactive substances may be modified by suitable dopants to achieve varying degrees of polarity and/or hydrophobicity, to achieve optimal adsorption and/or separation of targeted analytes.

Controller 119 may be electrically connected to each of the heater elements 125, 126, 127, 128, and detectors 115 and 118 as shown in FIG. 12. Controller 119 may energize heater elements 125, 126, 127 and 128 in a time phased sequence (see bottom of FIG. 14) such that each of the corresponding interactive elements 135, 136, 137, and 138 become heated and desorb selected constituents into a streaming sample fluid 111 at about the time when an upstream concentration pulse, produced by one or more upstream interactive elements, reaches the interactive element. Any number of interactive elements may be used to achieve the desired concentration of constituent gases in the concentration pulse. The resulting concentration pulse may be provided to detector 118, for detection and analysis.

FIG. 14 is a graph showing illustrative relative heater temperatures, along with corresponding analyte concentration pulses produced at each heater element. As indicated above, controller 119 may energize heater elements 125, 126, 127 and 128 in a time phased sequence with voltage signals 150. Time phased heater relative temperatures for heater elements 125, 126, 127, and 128 may be shown by temperature profiles or lines 151, 152, 153, and 154, respectively.

In the example shown, controller 119 (FIG. 12) may first energize first heater element 125 to increase its temperature as shown at line 151 of FIG. 14. Since first heater element 125 is thermally coupled to first interactive element 135 (FIG. 13), the first interactive element desorbs selected constituents into the streaming sample fluid 111 to produce a first concentration pulse 161 (FIG. 14) at the heater element 125, if no other heater elements were to be pulsed. The streaming sample fluid 111 carries the first concentration pulse 161 downstream toward second heater element 126, as shown by arrow 162.

Controller 119 may next energize second heater element 126 to increase its temperature as shown at line 152, starting at or before the energy pulse on element 125 has been stopped. Since second heater element 126 is thermally coupled to second interactive element 136, the second interactive element also desorbs selected constituents into streaming sample fluid 111 to produce a second concentration pulse. Controller 119 may energize second heater element 126 such that the second concentration pulse substantially overlaps first concentration pulse 161 to produce a higher concentration pulse 163, as shown in FIG. 14. The streaming sample fluid 111 may carry the larger concentration pulse 163 downstream toward third heater element 127, as shown by arrow 164.

Controller 119 may then energize third heater element 127 to increase its temperature as shown at line 153 in FIG. 14. Since third heater element 127 is thermally coupled to third interactive element 137, third interactive element 137 may desorb selected constituents into the streaming sample fluid to produce a third concentration pulse. Controller 119 may energize third heater element 127 such that the third concentration pulse substantially overlaps larger concentration pulse 163 provided by first and second heater elements 125 and 126 to produce an even larger concentration pulse 165. The streaming sample fluid 111 carries this larger concentration pulse 165 downstream toward an "Nth" heater element 128, as shown by arrow 166.

Controller 119 may then energize "N-th" heater element 128 to increase its temperature as shown at line 154. Since "N-th" heater element 128 is thermally coupled to an "N-th" interactive element 138, "N-th" interactive element 138 may desorb selected constituents into streaming sample fluid 111 to produce an "N-th" concentration pulse. Controller 119 may energize "N-th" heater element 128 such that the "N-th" concentration pulse substantially overlaps larger concentration pulse 165 provided by the previous N-1 interactive elements. The streaming sample fluid may carry the resultant "N-th" concentration pulse 167 to either a separator 102 or a detector 118.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A fluid analyzer system comprising:
a structure for holding a fluid-component sensitive material;
a first light conveyance situated in the structure;
a second light conveyance situated in the structure; and
a fluid conveyance situated in the structure; and
wherein:
the fluid conveyance has a sample inlet proximate to a defined spot on the fluid-component sensitive material, the fluid conveyance configured to direct flow of the sample fluid to be analyzed through the inlet and through the spot on the fluid-component sensitive material;
the fluid-component sensitive material is permeable to fluid and fluid-components; and
the spot on the fluid-component sensitive material through which the fluid conveyance directs the fluid is a micro-spot.

2. The system of claim 1, wherein:
the fluid-sensitive material comprises a paper- or polymer-like micro-porosity for hosting a reagent and providing reasonably uniform color changes within the area; and
the micro-spot has outside dimensions less than one millimeter.

3. The system of claim 1, further comprising:
a light source connected to the first light conveyance; and
a light detector connected to the second light conveyance: and
wherein:
the light source is for impinging light at the spot on the fluid-component sensitive material via the first light conveyance; and
the light detector is for detecting light scattered, transmitted and/or reflected from the spot on the fluid-component sensitive material.

4. The system of claim 3, wherein the light detector comprises a color discriminator such as a narrow wavelength band detector, an optical spectrometer, or the like.

5. The system of claim 1, further comprising:
a pre-concentrator having an input for a sample and having an output; and
a reservoir having an input connected to the output of the pre-concentrator and having an output connected to the fluid conveyance.

6. The system of claim 5, further comprising:
a pump having an input: and
a bypass conveyance connected between the output of the pre-concentrator and the input of the pump.

7. The system of claim 6, wherein:
the structure, for holding the fluid-component sensitive material, has an output connected to the input of the pump;
the reservoir is a rapidly heatable reservoir for pulling each of a plurality of pre-concentrated delta-time peaks of fluid into a high concentration path by slow heating and rapid cooling. and providing a high concentration fluid at a first flow rate from the output of the reservoir to the fluid conveyance mechanism;

the bypass conveyance is for providing a low concentration fluid at a second flow rate to the input of the pump; and the second flow rate is greater than the first flow rate.

8. The system of claim 5, wherein the pre-concentrator comprises an adsorber.

9. A fluid analyzer system comprising:

a structure for holding a fluid-component sensitive material:

a first light conveyance situated in the structure:

a second light conveyance situated in the structure: and a fluid conveyance situated in the structure; and wherein:

the fluid conveyance has an inlet proximate to a defined spot on the fluid-component sensitive material. the fluid conveyance configured to direct flow of the fluid through the inlet and through the spot on the fluid-component sensitive material;

the fluid-component sensitive material is permeable to fluid and fluid-components; and the spot on the fluid-component sensitive material through which the fluid conveyance directs the fluid is a micro-spot; and wherein the structure is an upper structure, the system further including a lower structure, wherein the upper and lower structures are configured to clamp the fluid-component sensitive material therebetween.

10. The system of claim 9, where the lower structure includes a fluid outlet, where the fluid conveyance directs flow of the fluid through the inlet, through the spot on the fluid-component sensitive material, and through the outlet in the lower structure.

11. The system of claim 2, wherein the micro spot has an outside dimension between one micron and one millimeter.

12. A fluid analyzer system comprising:

a first structure having first and second light conveyances and a fluid inlet;

a second structure having a fluid outlet, wherein the first and second structures are configured to clamp a fluid-component sensitive material therebetween;

wherein:

the first and second structures arc aligned such that the inlet is positioned to direct fluid flow through the fluid-component sensitive material at a defined spot and into the fluid outlet:

the fluid-component sensitive material is permeable to fluid and fluid-components: and the defined spot on the fluid-component sensitive material is a micro-spot.

13. The system of claim 12, wherein the micro-spot has outside dimensions less than one millimeter.

\* \* \* \* \*